United States Patent
Kober et al.

(10) Patent No.: US 7,459,483 B2
(45) Date of Patent: Dec. 2, 2008

(54) METHOD AND DEVICE FOR DETECTING FUMIGANTS IN AIR SAMPLES

(75) Inventors: Reiner Kober, Fussgoenheim (DE);
Wolf Stegmaier, Boehl-Iggelheim (DE);
Hans Ziegler, Mutterstadt (DE); Erich Probeck, Bockenheim (DE); Thomas Christen, Dannstadt-Schauernheim (DE); Joachim Bargon, Bonn (DE); Fritz Voegtle, Alfter-Impekoven (DE); Gerhard Horner, Wolfratshausen (DE)

(73) Assignee: Kanesho Soil Treatment SPRL/BVBA, Brussels (BE)

( * ) Notice: Subject to any disclaimer, the term of this patent is extended or adjusted under 35 U.S.C. 154(b) by 738 days.

(21) Appl. No.: 10/469,252

(22) PCT Filed: Feb. 28, 2002

(86) PCT No.: PCT/EP02/02206

§ 371 (c)(1),
(2), (4) Date: Aug. 28, 2003

(87) PCT Pub. No.: WO02/068953

PCT Pub. Date: Sep. 6, 2002

(65) Prior Publication Data

US 2004/0079651 A1    Apr. 29, 2004

(30) Foreign Application Priority Data

Feb. 28, 2001    (DE) ................... 101 09 534

(51) Int. Cl.
*A01N 47/40*    (2006.01)

(52) U.S. Cl. .................................... 514/514
(58) Field of Classification Search ............ None
See application file for complete search history.

(56) References Cited

U.S. PATENT DOCUMENTS 2,838,389 A    6/1958    Yoder (Continued)

FOREIGN PATENT DOCUMENTS

GB    590368    7/1947

(Continued)

OTHER PUBLICATIONS

C. Heil, et al., "Highly selective sensor materials for discriminating carbonyl compounds in the gas phase using quartz microbalances", Sensors and Actuators B, vol. 61, 1999, pp. 51-58.

(Continued)

*Primary Examiner*—Neil Levy
(74) *Attorney, Agent, or Firm*—Oblon, Spivak, McClelland, Maier & Neustadt, P.C.

(57) ABSTRACT

The present invention relates to a method and a device for detecting fumigants in air samples. The device can be designed for example as a portable analyzer 10 equipped with a stab probe 11 for sampling soil air. There are provided detection means 16 which, upon contact with the air sample, generate electrical signals which depend on the concentration of the fumigants to be detected in the air sample. In accordance with the invention, the detection means 16 comprise at least one mass-sensitive sensor, for example an array of quartz microbalances, which have suitable selective surface layers.

6 Claims, 4 Drawing Sheets

U.S. PATENT DOCUMENTS

| | | | |
|---|---|---|---|
| 5,332,580 | A | 7/1994 | Young et al. |
| 5,469,369 | A | 11/1995 | Rose-Pehrsson et al. |
| 6,085,576 | A | 7/2000 | Sunshine et al. |

FOREIGN PATENT DOCUMENTS

| | | |
|---|---|---|
| GB | 2 165 948 | 4/1986 |
| WO | WO 99/66304 | 12/1999 |
| WO | WO 00/78204 | 12/2000 |

OTHER PUBLICATIONS

J. R. Stetter, et al., "New sensor arrays and sampling systems for a modular electronic nose", Sensors and Actuators B, vol. 69, No. 3, XP-004218245, Oct. 25, 2000, pp. 410-419.

S.Y. Szeto, et al., "Nonpoint-Source Groundwater Contamination by 1,2,2-Trichloropropane, a Trace Impurity in Soil Fumigant Formulations", Journal of Environmental Quality, vol. 23, No. 6, XP-002206312, Nov. 1994, pp. 1367-1370.

Patent Abstract of Japan, JP 2001-031510, Feb. 6, 2001.

DeQuan Li, et al., "Surface acoustic wave microsensors based on cyclodextrin coatings", Sensors and Actuators B, vol. 69, No. 1-2, XP-004208562, Sep. 10, 2000, pp. 75-84.

E. Souteyrand, et al., "Behaviour of Cryptophane Molecules in Gas Media", Transducers 95, Eurosensors IX, XP-010304938, Jun. 25-29, 1995, pp. 882-885.

Andreas Hierlemann, et al., "Polymer-based sensor arrays and multicomponent analysis for the detection of hazardous organic vapours in the environment", Sensor and Actuators B, vol. 26-27, XP-002204810, 1995, pp. 126-134.

E. Dalcanale, et al., "Selective detection of organic compounds by means of cavitand-coated QCM transducers", Sensors and Actuators B, vol. 24, No. 1-3, XP-004302098, 1995, pp. 39-42.

Paul G. Forsith, et al., "Preliminary field trials using the solid fumigant Basamid amended with selected additives", Forest Products Journal, vol. 43, No. 2, Feb. 1993, pp. 41-44.

A. Ufer, et al., "Impact of the Soil Disinfectant NT Basamid Granular on Terrestrial Non-Target Organisms", Acta Horticulturae 382, 1995, pp. 110-118.

Paul G. Forsyth, et al., "Decomposition of Basamid in Douglas-Fir Heartwood: Laboratory Studies of a Potential Wood Fumigant", Wood and Fiber Science, vol. 27, No. 2, Apr. 1995, pp. 183-197.

J. Gan, et al., "Transformation of 1,3-Dichloropropene in Soil Thiosulfate Fertilizers", Journal of Environmental Quality, vol. 29, No. 5, Sep.-Oct. 2000, pp. 1476-1481.

Periyasamy Subramanian, et al., "Degradation of 3,5-Dimethyl-Tetrahydro-2H-1,3,5-Thiadiazine-2-Thione in Aqueous Aerobic Media", Environmental Toxicology and Chemistry, vol. 15, No. 4, 1996, pp. 503-513.

E. J. Brouwer, et al., "Personal air sampling and biological monitoring of occupational exposure to the soil fumigant Cis-1,3-dichloropropene", Occupational Environmental Medicine, vol. 57, No. 11, 2000, pp. 738-744.

Krishna K. Verma, "Determination of Alkyl Thioureas, Isothiocyanates and Amines with Iodine Monochloride", Bulletin of the Chemical Society of Japan, vol. 52, No. 7, Jul. 1979, pp. 2155-2156.

Emmanuel I. Iwuoha, et al., "Reactivities of Organic-Phase Biosensors. 1. Enhancement of the Sensitivity and Stability of Amperometric Peroxidase Biosensors Using Chemically Modified Enzymes", Analytical Chemistry, vol. 69, No. 8, Apr. 15, 1997, pp. 1674-1681.

K. Nakamura, et al., "Classification and Evaluation of sensing films for QCM odor sensors by steady-state sensor response measurement", Sensors and Actuators B 69, 2000, pp. 295-301.

Albert Ehlen, et al., "Organic Clathrate-Forming Compounds as Highly Selective Sensor Coatings for the Gravimetric Detection of Solvent Vapors", Angew. Chem. Int. Ed. Engl., vol. 32, No. 1, 1993, pp. 110-112.

P. Boeker, et al., "Monolithic sensor array based on a quartz microbalance transducer with enhanced sensitivity for monitoring agricultural emissions", Sensors and Actuators B 70, 2000, pp. 37-42.

Von Fritz Voergtle, et al., "Einstufige Synthese eines vierfach funktionalisierten Catenans", Angew. Chem., vol. 104, No. 12, 1992, pp. 1628-1631.

Fritz Voergtle, et al., "One-Step Synthesis of a Fourfold Functionalized Catenane", Angew. Chem. Int. Ed. Engl., vol. 31, No. 12, 1992, pp. 1619-1622.

Stephan Ottens-Hildebrandt, et al., "Amide-based Furano-catenanes: Regioselective Template Synthesis and Crystal Structure", J. Chem. Soc., Chem. Commun., 1995, pp. 777-778.

METHOD AND DEVICE FOR DETECTING FUMIGANTS IN AIR SAMPLES

The present invention relates to a method and device for detecting fumigants in air samples.

The soils used in agriculture or horticulture can be infested with plant-injurial organisms, also known as phytopathogens, such as nematodes, soil-dwelling insects, germinating plants, soil bacteria or soil fungi. For example, the yield loss resulting from the attack of useful plants by soil-dwelling nematodes or root-knot nematodes are estimated at approx. 12% worldwide, which corresponds to a loss of income for the producers of at least 7 billion US dollars. Moreover, international plant quarantine regulations stipulate that the plant material being exported and imported be free from nematodes but also that it be grown in nematode-free soils. It is therefore frequently necessary to disinfest/disinfect agriculturally used soils before the next planting or replanting, for example by treatment with a fungicide or a nematicide.

In most cases, what are known as fumigants (smoke generators or gas-generating products for the soil) are employed for soil disinfestation/disinfection. Fumigants are usually applied in liquid form or in solid form. While liquid formulations act in the soil owing to their high vapor pressure, solid compounds which are introduced into the soil in the form of, for example, granules, disintegrate in the presence of soil moisture into gaseous, biocidally active compounds. The preparations diffuse through the soil's capillary system, where they come into contact with the pests and act as a respiratory poison. Fumigants may also act as contact poisons upon direct contact.

In recent decades, methyl bromide was the most widely used gas-generating product for the soil. However, methyl bromide is known to be a substance which contributes to damaging the earth's ozone layer. This is why, in 1997, over 100 countries decided, in a follow-up conference to the "Montreal Protocol on Substances that Deplete the Ozone Layer" that methyl bromide must no longer be employed from 2005 in industrial states and from 2015 in developing countries. In 1998, the US Congress, in harmonization with the "Montreal Protocol", postponed until 2005 a ban of methyl bromide already intended to be in force in 2001.

This is why other soil disinfestants/disinfectants are increasingly being considered in place of methyl bromide.

Thus, U.S. Pat. No. 2,838,389 describes the use of tetrahydro-3,5-dimethyl-1,3,5-thiadiazine-2-thione, of the formula common name "dazomet" as a product for the disinfestation/disinfection of soils in agriculture and horticulture. When dazomet is applied, methyl isothiocyanate (MITC), of the formula is released as the actual bioactive agent. Dazomet itself therefore only constitutes what is known as a prodrug precursor. In the more recent literature, the soil disinfestation/disinfection with dazomet in the form of Basamid® granules (Basamid is a registered trademark of BASF AG, Ludwigshafen) is described in *Forest Prod. J.* 43(2) (1993), pp. 41-44; in *Acta Horticulture* 382 (1995) pp. 110 et seq. and in *Fand Fiber Science* 27(2) (1995), pp. 183-197.

Basamid® granules are a relatively inert solid material which becomes active only upon application to the damp soil. Preferred fields of application for Basamid® are the production of ornamentals, vegetables and tobacco, tree nurseries, fruit, wine and hop production, and the disinfestation/disinfection of compost and greenhouse soil. Basamid® granules, which comprise 98 to 100% dazomet, are applied by spreading and are incorporated into the soil at a depth of 20 to 30 cm, but, if required, also up to a depth of 50 cm. The soil is subsequently usually covered with plastic sheeting to keep it damp during the treatment time and to avoid unduly early losses of the gaseous active component.

Another liquid soil disinfestant/disinfectant which, like dazomet, releases MITC is sodium methylcarbamodithionate, which is sold under the trade names VAPM, METHAM-FLUID, AAMONAN or DICID. Also, MITC is frequently employed directly or as a formulation under the trade names TRAPEX and VORAX for gassing. It may also be used as a mixture with metham. The agent is typically employed as a 20% strength solution in an organic solvent, which is intended to enhance the volatility of the active ingredient.

Another liquid soil disinfestant/disinfectant and nematicide is 1,3-dichloropropene (1,3-DCP), which is sold under the trade names DCP 50, SCHELL-DD, TELONE or DI-TRAPEX and which may also be employed in combination with MITC.

The known gas-generating products for the soil exhibit high phytotoxicity. They can therefore be employed only where the crops have already been cleared from the area to be treated. After each use of a soil disinfestant/disinfectant, a certain time must elapse before new useful plants and crop plants can be sown or planted in order to ensure that there is no danger of adverse effects on the newly-sown or newly-planted crops.

However, relatively little is known about the activation, release and degradation of the bioactive substances of the above-mentioned gas-generating products for the soil. Important factors which affect the metabolism of the gas-generating products in the soil are, however, temperature, water content and pH of the soil. The soil type too, for example the presence of transition metals, plays a certain role in this context.

Likewise, the application of fertilizers and other substances has a considerable effect on the rate at which gas-generating products for the soil are released from the soil. Thus, it has only been shown recently that fertilizers comprising thiosulfates reduce the volatility of 1,3-DCP, which is normally high (Gan et al., *Journal of Environmental Quality* 29(5) (2000), pages 1476-1481).

Owing to this multiplicity of factors, the MITC or 1,3-DCP concentration in the soil as a function of time in the case of a specific application cannot be estimated with a sufficient degree of accuracy unless measurements are carried out.

However, not only the knowledge of the exact residual MITC and 1,3-DCP content in the soil is important for the user, owing to the phytotoxicity of the substances, but monitoring the room air and ambient atmosphere is necessary for work safety reasons, owing to the toxic action of these substances. Thus, it has been shown that, when dazomet granules are employed, MITC is released very rapidly at high soil temperatures above 30° C. and sufficiently high soil moisture. In particular in the case of greenhouse applications, it has been observed, when the granules were incorporated into the soil, that the MITC released can lead to temporary irritations of the mucous membrane and eyes when ventilation and use are inadequate. In this context, it is also known that metham fluid or metam-sodium can only be used within limits in the greenhouse since they tend to evolve gas very rapidly and in great quantities or that they are no longer approved for such applications as is the case for example in California. Without a rapid and reliable determination method there exists therefore the risk of agricultural workers and other users being exposed to the MITC or 1,3-DCP released for an unnecessarily long time or to an unduly high concentration of these gases.

A variety of HPLC and GC methods are known as analytical or chromatographic methods for detecting the soil gases MITC and/or 1,3-dichloropropene (cf., for example, Subramanian, *Environm. Toxicol. Chem.* 15 (1996), pages 503-513). Thus, for example, the detection of the exposure of agricultural workers in potato production to the nematicide cis-1,3-dichloropropene (cis-DCP) and the determination of its effect on humans have hitherto been carried out by urine analyses. Only recently has it been found in a Dutch study that the legal upper limit of the daily exposure was exceeded on over 20% of the days during the observation period (Brouwer et al., *Occupational and Environmental Medicine*, 57(11) (2000), pages 738-744).

Chemical, in particular wet-chemical, organic and inorganic detection methods of isothiocyanates are likewise known. Thus, *Bull. Chem. Soc. Jap.* 52, (1979), pages 2155-2156 discloses the detection of isothiocyanates with iodine monochloride by the formation of alkylthioureas by reacting the isothiocyanates with alkylamine.

However, these detection methods are either not sensitive enough or so complicated that they can only be carried out in well-equipped laboratories. These methods are therefore not suitable for the day-to-day use by the user of crop protection products.

After the application of metam-sodium, 1,3-dichloropropene and/or dazomet has been applied, however, it is particularly important for the user to test for the presence of residual amounts of MITC and/or 1,3-DCP in the soil which have not yet been mineralized or degraded. If this is the case, the user must wait for a certain time to elapse since residual amounts of these materials in the soil can lead to plant damage when new useful plants and crop plants are sown or planted. When using the solid product dazomet, in particular, the detection of MITC is particularly important since as has already been described above the release and mineralization of MITC is greatly affected by soil structure, temperature, moisture, type and concentration of fertilizer and other factors.

As a rule, users currently employ a biotest system with cress or tobacco seeds, which has been developed specifically for on-site application. It is based on the fact that these seeds are inhibited from germinating by minute amounts of MITC and therefore indirectly indicate residual MITC. However, this test, which is known as the cress test, is complicated and requires, in turn, several days to elapse until it can be demonstrated that, for example, the cress emerges, that is to say establishes itself. A further disadvantage of such biotests is the false-positive or false-negative detection or indication of MITC for example by flawed water management.

From international patent application WO99/66304 a method and a device for trace level detection of analytes using artificial olfactometry is known. While being preliminarily concerned with medical applications such as detecting halitosis and periodontal disease, numerous other fields of applications, including detection of fumigants, and numerous different sensor types are briefly mentioned. However, except from suggesting to provide a fluid concentrator, WO99/66304 does not disclose any technical teaching how trace levels of analytes can reliably be detected in air samples. Especially, said document is not concerned with detection of MITC or 1,3-DCP.

A biosensor for the sensory detection of methyl isothiocyanate (MITC) has already been developed (Iwuoha et al. *Analytical Chemistry*, 69(8) 1674-1681 (1997)). This biosensor employs amperometric enzyme electrodes which operate in liquid organic phases (OPEEs=organic phase enzyme electrodes). Owing to their availability, these compounds which qualify as substrates for oxidoreductases can be detected in a suitable solvent, i.e. in liquid phase, without requiring complicated sample preparation. Prior to the availability of OPEEs, it was only possible to detect those analytes which are soluble in water. However, the sensor signals delivered by the OPEEs are considerably weaker than the sensor signals yielded in water by electrodes which have natural enzymes immobilized on them. According to Iwuoha et al. (above), the sensitivity of the OPEEs can be improved in two ways: either natural enzymes are used in a solvent mixture composed of an organic medium (for example acetonitrile, $CH_3CN$), and water, or the natural enzymes are modified by altering their amino acid units, i.e. artificial enzymes are used. Each of two biosensor types described by Iwuoha et al. uses one of the two principles. Horseradish peroxidase (HRP) acts universally as basal enzyme. This enzyme reacts with $H_2O_2$ and gives rise to a sensor signal. However, since MITC inhibits HRP, an existing concentration of MITC alters the response behavior of the suitably coated biosensor towards a particular $H_2O_2$ concentration. Modified enzymes which are adapted for this purpose are either an HRP which is modified with the homobifunctional agent suberic acid bis(N-hydroxysuccinimidate) to give SA-NHS, or an enzyme modified with ethylene glycol bis(N-hydroxysuccinimidate) to give EG-NHS. The electrodes were prepared with the aid of an electrostatic complexing technique described in the literature.

However, the known MITC biosensor is not suitable for use in agricultural and horticultural practice since the gaseous analyte must first be dissolved in a suitable solvent and then, in dissolved form, makes contact with the actual sensor. Such a sensor is not only expensive to prepare, owing to the containers required for fresh and used solvents, for wash liquids and purge gases and the corresponding complicated arrangement of lines, but is also very heavy and very complicated and delicate to handle, so that it is not suitable for a mobile analytical device. Moreover, the detection sensitivity which can be achieved is too low for use in agriculture and in horticulture.

It is an object of the present invention to address the technical problem of providing a simple and reliable method of detecting fumigants in air samples, which method can be employed on site by the user of soil disinfestants/disinfectants, be it in agriculture or in market gardens, and which is sufficiently sensitive for reliably and accurately detecting residual amounts of fumigants in soil air or ambient air. In particular, it is intended that, by using the method according to the invention, risks arising in new sowings or new plantings of useful plants and crop plants, for example following the application of Basamid or 1,3-dichloropropene, are avoided without the user having to resort to the complicated and time-consuming cress test which has hitherto been used. Also, it is intended to provide a method of controlling phytopathogens with soil disinfestants/disinfectants which permit a more reliable and more controlled use of the soil disinfestants/disinfectants. Finally, it is intended to provide an inexpensive and compact device for detecting fumigants in air samples which device can be used without knowledge of analytical chemistry and which can be employed as a light and compact analytical portable device.

We have found that this object is achieved by measuring fumigants in air samples by means of chemosensors. Chemosensors are sensors which convert a measurable variable which is specific for a chemical substance into a signal, in particular an electrical signal, capable of evaluation. Such sensors can be based on different physical principles of measurement. For example, a semiconductor element, such as a metal oxide semiconductor (MOS) or a metal oxide semiconductor field effect transistor (MOSFET), but also electrically conductive polymers which are known as conducting polymer sensors (CPS) may act as the sensitive sensor element. Surprisingly, it has now been found that mass-sensitive sensors which are coated with a surface layer which is selective for the fumigants to be detected, are very especially suitable for detecting fumigants in air samples at the sensitivity level required for use in agriculture and horticulture.

Mass-sensitive sensors are known, for example, as "quartz micro-balances" (QMBs) or as "surface acoustic-wave devices" (SAWs). Quartz micro-balances are employed for example in coating plants, for example sputtering plants, for monitoring the coating thickness. Usually, a crystal oscillator is integrated into an electrical resonant circuit. The quartz crystal makes contact with metal electrodes and, exploiting the reverse piezoelectric effect, stimulated at a frequency, typically in the radio frequency range, which corresponds to a mechanical natural frequency of the crystal. This results in the stimulation of resonant oscillations, which determine a stable oscillation frequency of the resonant circuit. The resonant frequency now depends on the mass of the crystal oscillator, so that mass changes, for example owing to absorption or adsorption of an analyte, can be detected as changes in the resonant frequency. Frequency changes in the range of 1 Hz can be measured by electrical bridge circuits.

Thus, the present invention relates to a method of detecting fumigants in air samples, wherein an air sample is drawn in, the drawn-in air sample makes contact with at least one mass-sensitive sensor, said mass-sensitive sensor being coated with a surface layer which is selective for the fumigants to be detected, mass changes of the sensor are detected in the form of electrical signals, and the electrical signals are evaluated.

In accordance with the invention, fumigants can be detected, for example in soil air from soils which have been treated with soil disinfestants/disinfectants. To monitor the exposure of agricultural workers or workers in greenhouses, the mass-sensitive sensor can also be used for detecting fumigants in air in the vicinity of the soil, preferably up to a level of 1 to 3 m above ground or in room air, in particular in greenhouses.

The mass-sensitive sensor is especially preferably used for detecting MITC and/or 1,3-dichloropropene (1,3-DCP). However, the mass-sensitive sensor can also be used for detecting other gaseous fumigants, in particular for detecting methyl bromide.

The sensor is equipped with a coating which is as selective as possible for the substance to be detected, for example MITC. Ideally, therefore, a single sensor with a highly-specific coating will suffice to detect the substance of interest. However, a multiplicity of different substances is present in air samples, in particular soil air from the agricultural sector. Besides the gases present in atmospheric air, soil air shows increased $CO_2$ contents (typically 0.3-3.0, in some cases up to 10% by volume), mainly as a consequence of the degradation by microorganisms of degradable organic substances. In addition, other gases are also formed in soils, mainly by microbial processes. Depending on the substances present, and the Eh-pH conditions of the various soils, which differ from season to season, these are, for example, $N_2O$, $NO$, $NO_2$, $NH_3$, $SO_2$, $H_2S$, $CH_4$, $C_2H_4$, and other substances with a relatively high vapor pressure. Moreover, depending on the degree of pollution of the ambient air and of the soils, the presence of volatile organic compounds such as fuels, solvents and others from anthropogenic sources must be expected to be found in the soil air. Approximately 15 years ago, tetrachloroethylene contents in the soil air of from 0.1 to 112 $\mu g/m^3$ and similarly increased trichloroethene and trichloroethane contents were measured even in largely unpolluted soils in southern Germany.

Usually, coated mass-sensitive sensors exhibit a more-or-less pronounced sensitivity for individual, but normally several, components of a gas mixture. Chemosensors frequently exhibit a similar degree of sensitivity to substances of a related nature owing to what is known as cross sensitivities. To differentiate between these substances, or to detect unambiguously just a single chemical compound, a plurality of sensors in a suitable combination, known as sensor arrays, are therefore usually required. Such systems based on a wide range of chemosensory measuring principles have already been described in the literature under the name "electronic noses" for applications other than the detection of fumigants.

Therefore, it will be preferred in accordance with the invention to use a plurality of sensors which are preferably coated with different selective layers. In principle, the less specific the coatings of individual sensors are for the substances to be detected and the broader the range of application of the sensor array is to be, the more sensors will be required. To detect fumigants, in particular to detect a few substances such as, for example, MITC or 1,3-DCP, preferably two to twelve, in particular approximately six, different sensors are employed.

However, the selective coatings described hitherto in the literature are either unsuitable or not sensitive enough for detecting fumigants in air samples. Selection criteria for the choice and combination of suitable layers are described, for example, by: Nakamura et al., *Sensors and Actuators B* 69/3, 295-301 (2000). Furthermore, piezoelectric sensor systems with gold electrodes and AT-cut quartz crystals are described which are coated with polydimethylsiloxane, polyetherurethane, polyethylcellulose or polycyanopropylmethylsiloxane and operated as an array composed of 4 piezoelectrical sensors. The crystals were located in a chamber which can be maintained at constant temperature and was equipped with a gas inlet and outlet. Data gathering, the gas mixture and its flow through the chamber were controlled by a personal computer. Standardization of the concentrations of the gases in the chamber and of the sensitivity of the sensors was performed by isothermal exposure at room temperature. The concentrations of the gases were 100 to 1 000 ppm in the case of toluene and chloroform and 250 to 2 000 ppm in the case of n-octane.

Surprisingly, it has now been found that a coating of the mass-sensitive sensor with macrocycles and/or dendrimers is a particularly suitable selective coating for detecting fumigants. Such coatings have already been described for example for the gravimetric detection of solvent vapors by Ehlen et al., *Angew. Chem., Int. Ed. English* 32, 111-112 (1993). Moreover, such selective coatings have been used for detecting carbonyl compounds in the gas phase, and ammonia.

The preferred field of application of the sensor according to the invention is the agricultural sector, where it is also intended to be used by operators less versed in the art of instrumentation. It is therefore desirable that the mass-sensitive sensor be especially robust, easy to handle and inexpensive. To allow highly-sensitive measurements to be performed nevertheless, the fumigants to be detected will, in an especially preferred embodiment of the method according to the invention, first be concentrated before making contact with the mass-sensitive sensor. To this end, for example, the soil gas can first be passed through an adsorber or absorber, for example made of silica gel or "TENAX", or else the analyte is first condensed and subsequently delivered to the sensor in concentrated form with the aid of an inert gas (for example air or nitrogen).

Advantageously, the moisture content of the air sample will additionally be determined, so that, for example in the case of unduly dry air, indications are obtained that the conversion of dazomet in the soil is insufficient. In the case of unduly dry air, for example, it is possible to indicate, by means of a signal, that the reading may be unreliable because more, unreacted dazomet may still be present in the soil.

To measure soil-air samples, for example, a probe can be inserted into the soil to a depth of several centimeters to several tens of centimeters, and a specific amount of air can be drawn in via the probe by means of a suction pump and passed past the mass-sensitive sensor. The substance to be detected is deposited on the mass-sensitive sensor and alters the resonant frequency of a resonance circuit into which the sensor is integrated.

According to another embodiment of the invention, a sample of soil to be tested, e.g. several 100 g, is filled into a vessel. Subsequently, air which includes fumigants released from the soil sample is drawn from the vessel into a measuring chamber which houses the sensor array.

In order to increase the accuracy of measurement, it is possible to remove moisture from the air sample before the air sample is drawn into the measuring chamber.

The present invention also relates to a method of controlling phytopathogens, which comprises treating the soil with an effective amount of a gas-generating product for the soil and subsequently detecting released fumigants by the above-described method using a mass-sensitive sensor.

The present invention further relates to a device for detecting fumigants in air samples with sampling means for taking an air sample, detection means which, upon contact with the air sample, generate electrical signals which depend on the concentration of the fumigants to be detected in the air sample, evaluation means which calculate the concentration of the fumigants present in the air sample on the basis of the electrical signals produced by the detection means, wherein the detection means of the device comprise at least one mass-sensitive sensor which is coated with a surface layer which is selective for the fumigants to be detected.

The mass-sensitive sensor can comprise for example a surface acoustic wave device. While changes in the mass occupancy can be measured very sensitively using surface acoustic wave devices, such sensors are also highly sensitive to temperature, so that extensive measures must be taken for maintaining a constant temperature of the resonators. Surface acoustic wave devices are therefore less suitable for the field of application in agriculture which is preferred for the purposes of the present invention. At least one quartz microbalance is therefore especially preferably employed as mass-sensitive sensor. The crystal resonator constitutes a piezoelectric resonator in an electrical resonant circuit. Changes in the mass in the resonator lead to a shift in resonant frequency of the resonant circuit, which can be evaluated electronically.

An array of mass-sensitive sensors of which at least one is a sensor coated with a surface layer which is selective for the fumigants to be detected is preferably used. Preferably, however, two or more sensors are coated with different selective layers and the signals obtained are evaluated by what are known as chemometrical methods.

The surface layer which is selective for the fumigants to be detected preferably comprises macrocycles, e.g. lactame amide type macrocycles, and/or dendrimers. It was found that by suitably tailoring the molecular composition of said macrocycles and/or dendrimers, a high selectivity of the layer for incorporation/adsorption of MITC or 1,3-DCP can be obtained.

In accordance with a preferred variant of the device according to the invention, at least one concentration unit for the fumigants to be detected is additionally provided.

Preferably, a moisture or vapor barrier is arranged in the fluid pathway upstream of the measurement chamber which is permeable for fumigants to be detected and impermeable for moisture contained in the air sample. Preferably, said moisture barrier comprises a linear low density polyethylene (LLDPE) foil. In an embodiment which includes a sample vessel for soil to be tested, the moisture barrier may be a LLDPE bag or in-liner which may be filled with soil. Typically, the thickness of the LLDPE foil will be between 5 and 50 µm, preferably 5-10 µm. Thus the disposable LLDPE bag will not only function as a moisture barrier but will also allow the sample vessel (e.g. a box made of stainless steel or another surface which does not retard fumigants) to remain clean after each use.

The detection device according to the invention can be produced to be especially robust and inexpensive and can also be designed together with a concentration unit to give a very compact device. In particular a portable analyzer can therefore be realized with the device according to the invention. For use in agriculture, for example, the analyzer can comprise a rod-like probe which can be stabbed into the soil for sampling.

Stationary analyzers which comprise transmitters which transmit readings, preferably by air, to a central data acquisition station, may also be designed.

The invention is described in greater detail hereinbelow with reference to the use example shown in the appended drawings.

Figure 1:
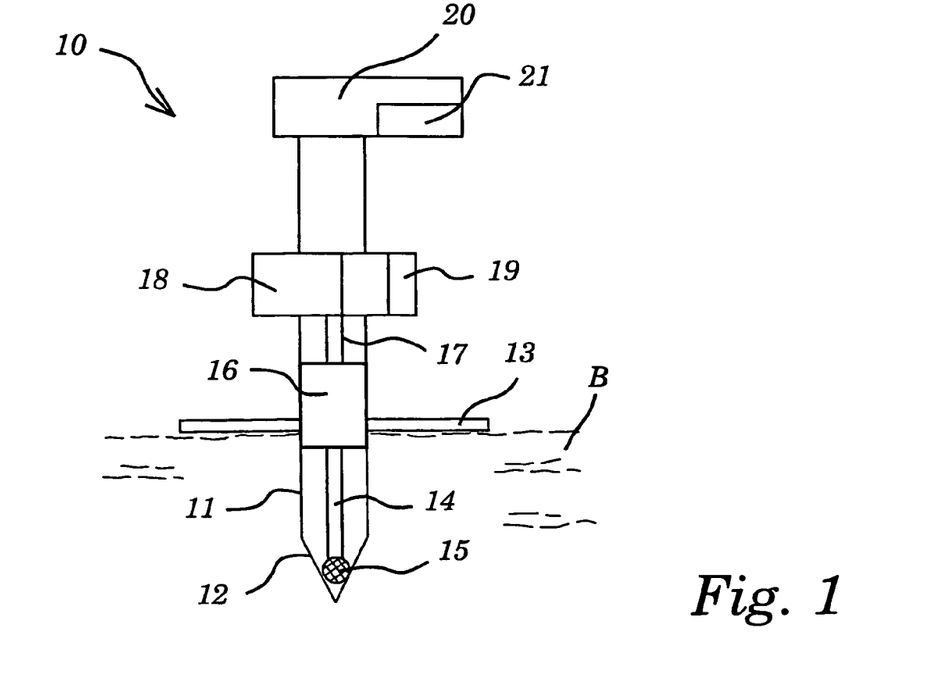
FIG. 1 shows a schematic representation of a portable analyzer according to the invention for detecting fumigants in the soil air.

FIG. 1 shows an embodiment of the device according to the invention for detecting fumigants in air samples. The device according to the invention is designed as a portable stab probe 10. The probe 10 has a shaft 11 which, with its tip 12, can be inserted into the soil B for sampling soil air. A collar-shaped sheet 13 which, upon insertion of the shaft into the soil, acts as a step is provided at the external circumference of the shaft 11 so that sampling is always effected at a defined depth. Provided within the shaft 11 is a line 14 which opens out into the external circumference of the shaft in the tip 12. The orifice of line 14 is covered by a fine mesh 15 which prevents soil or other solid particles being drawn in when soil air is drawn in. Line 14 leads to detection means 16, which comprise a measurement chamber in which there is arranged a quartz microbalance array for detecting fumigants. A preferred embodiment of the detection means 16 is illustrated in greater detail further below with reference to FIG. 2, which is shown in greater detail. An outlet line 17, which leads out of the detection means 16, opens into conveying means 18, which may be designed as, for example, a blower or a suction pump, and which convey the soil air via line 14 through the detection means 16. Moreover, one or more cartridges 19 with purging and/or calibrating gases can be provided. In the example shown, power supply means such as, for example, batteries 21, which supply the probe with electricity are arranged in a handle 20 on the probe 10.

The probe can exhibit suitable display units for visually and/or acoustically indicating the readings. Moreover, transmitting and receiving units for remote control and data transfer may be provided. Such units are known to the skilled worker and are not illustrated in greater detail in this context.

Figure 2:
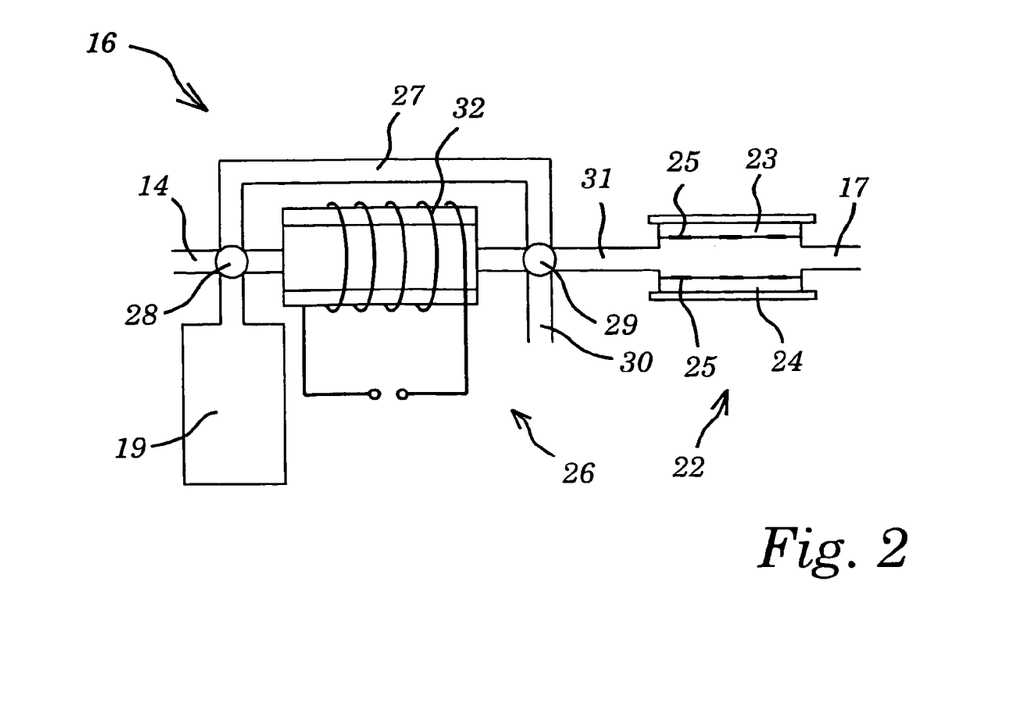
FIG. 2 shows a schematic representation of the measuring chamber of the analyzer of FIG. 1.

FIG. 2 is a schematic representation of a preferred embodiment of the detection means 16 with mass-sensitive sensors. As a matter of course, the detection means 16 can also be used when a sample vessel (not depicted) for soil is employed. The detection means 16 comprise a measuring chamber 22, which, in the example shown, is delimited above and below by crystal lamellae 23, 24. A plurality of metal spots 25, which define the individual sensors of the array, are vapor-deposited on the crystal lamellae. The individual sensors are coated with selective surface layers, for example by means of electrostatic spraying. Some of the coatings preferably have an especially high selectivity for the fumigants to be detected. One or more sensors may also be coated with a material which is insensitive to the fumigants to be detected, but especially sensitive to the moisture present in the air. A preferred moisture-sensitive material is, for example, polyvinylpyrrolidone (PPy). One or more sensors may also be uncoated or provided with an especially inert coating which is sensitive neither to moisture nor to other components of the soil gas. Such sensors are in particular suitable for monitoring any drift in the evaluation electronics, as can occur for example owing to variations in temperature. A more detailed representation of such a sensor system, in particular a description of advantageous measuring modes when determining the concentration of gases is found in Boeker et al. *Sensors and Actuators B* 70 (2000), 37-42. The construction of the individual sensor elements is illustrated in greater detail hereinbelow in connection with the representation of FIG. 3.

In the example shown in FIG. 2, a concentration unit 26 is arranged upstream of the measuring chamber 22. If, for example, it is only intended to determine the moisture in the soil, or if the fumigants to be detected are present in higher concentrations, the concentration unit can also be bypassed via a bypass 27. The flow routes are controlled via suitable valve units 28, 29, which are controlled automatically by a control unit (not shown). To carry out a measurement with upstream concentration, soil air is first conveyed via the line 14 through the concentration unit 26 and the line 30 to the pump 18 (not shown in FIG. 2). The connecting line 31 to the measuring chamber 22 is shut. The concentration unit 26 may have arranged in it for example silica gel or TENAX as adsorbent or absorbent. After a given concentration period, line 30 is shut and line 31, leading to the measuring chamber 22, is opened. The absorbed/adsorbed material is desorbed thermally via a heater 32 and transferred from the concentration unit 26 into the measuring chamber 22 with the aid of the conveying pump and/or a purge gas located in cartridge 19. In certain embodiments of the invention, a moisture barrier 46, e.g. a LLDPE foil, is provided upstream of the measurement chamber 22.

Figure 3:
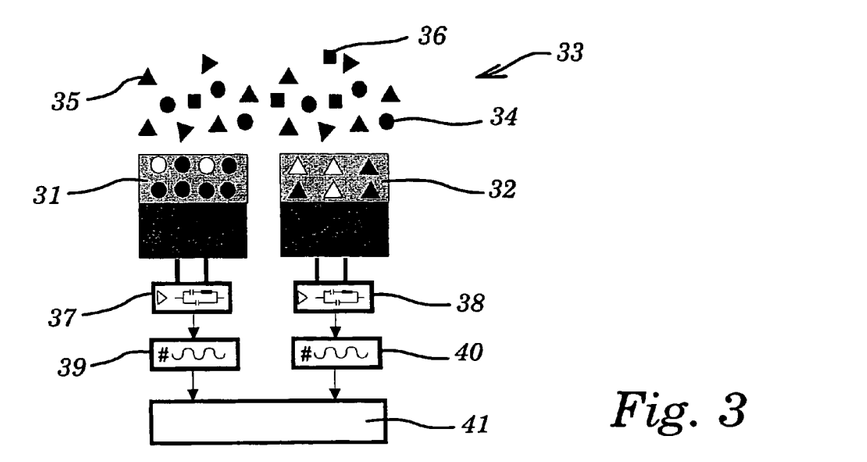
FIG. 3 shows a schematic representation of two mass-sensitive sensor elements with selective surface layer as are used in the measuring chamber of FIG. 2.

The measuring principle of a quartz microbalance, which is used in accordance with the invention for detecting the fumigants, is known to the skilled worker from other fields of analytics and will therefore only be mentioned briefly with reference to the representation of FIG. 3. Each individual element of the sensor array (two of these elements are shown in FIG. 3) exhibits a selective surface layer 31, 32, which differ with regard to their sensitivity for the individual components of the soil air sample 33 (shown symbolically as circles 34, triangles 35 or rectangles 36). For example, layer 31 is sensitive specifically for the air components with the circles 34 as symbols, while layer 32 is sensitive specifically for the air components shown as triangles 35. A change in the mass in the individual sensor elements by the adsorption or absorption of components of the air sample is evaluated by a change in the resonant frequency of an oscillator circuit 37, 38, which is shown schematically, via frequency counters 39, 40. However, in reality, the individual sensor elements are never one hundred percent selective. Thus, for example, when carrying out an actual measurement, sensor element 31 will also respond to a certain extent to the air constituents 35 and 36. The readings provided by the individual sensor elements 31, 32 are therefore subjected to an electronic signal evaluation stage 41, which is arranged downstream and which determines the concentrations of the individual components in the soil-air sample 33 by means of chemometric methods which are known per se.

Surprisingly, it has been found that supramolecular systems are particularly suitable as selective coatings 31, 32 for detecting fumigants in air samples. In particular what are known as macrocycles and dendrimers are attractive, owing to their monodispersivity, since they allow the construction of reversible, rapidly responding and regenerable gas sensors. Furthermore, owing to their cavities which can be designed in many ways and adapted specifically to the spatial requirements of the analyte to be detected, they allow great variety and freedom of design. By exploiting the host-guest-interaction, to which individually formed hydrogen bridges also contribute, or by exploiting a specific donor-acceptor interaction, individually tailored host systems can be synthesized. Supramolecular host systems allow to a particular extent the ideal adaptation to the host in question since, for example, dendrimers exhibit a high tolerance for various types of functional groups.

Figure 4:
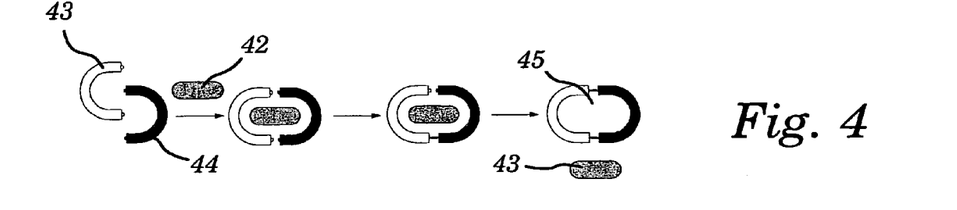
FIG. 4 shows an example of a synthetic principle for supramolecular units for selective surface layers.

FIG. 4 shows the synthetic principle of supramolecular units on the nanometer scale as an example, a guest molecule 42 acting as template for the circularization of two supramolecular units 43, 44 to give the host molecule 45. The specific synthesis of attractive hosts 45 is made possible in this manner, whose suitability as substrate-selective layer systems for the fumigants of interest in the present context can be tested and optimized with the aid of the device according to the invention.

Figure 5:
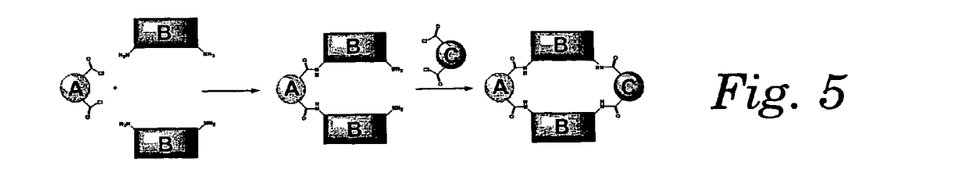
FIG. 5 shows a schematic synthetic strategy for macrocycles of selective surface layers.

FIG. 5 shows an example of a synthetic strategy for macrocycles, which are also suitable as selective surface layer. The highly-flexible synthetic strategy for the preparation of the macrocycles has proved to be particularly advantageous. Not only the lateral moieties A, C of what is to become the macrocycle, but also the spacers B can be varied independently of one another. This makes it possible to preset the type and strength of the host-guest-interaction in a targeted fashion. This means that these host molecules can be adapted without complications to what is to become their task as sensor-active layer.

Both thermodynamic and kinetic parameters of the intercalation processes for the adsorption and desorption of specific guest molecules can be determined. The information obtained can be used for the optimization or precise differentiation between related species of guest molecules, so that the selectivity and sensitivity of the sensor-active layers of the device according to the invention for the detection and the differentiation of related species of carbonyl compounds can be improved substantially. As regards the chemistry of the macrocycles and catenanes, reference may be made in particular to the pioneering work of Vögtle et al. *Angew. Chem.* 104 (1992), 1628-1631; *Angew. Chem. Int. Ed. Engl.* 31 (1992), 1619-1622. Synthetic strategies are also found for example in Ottens-Hildebrandt et al. *J. Chem. Soc., Chem. Commun.* (1995), 777-779.

Figure 6:
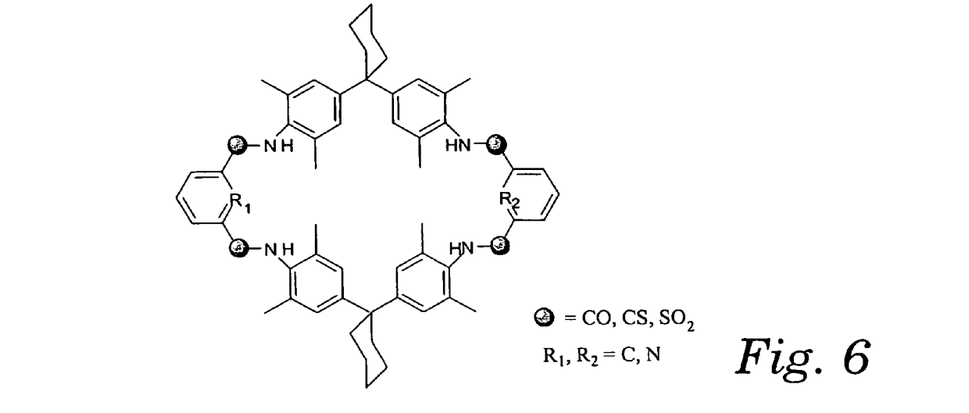
FIG. 6 shows an example of a macrocycle which is suitable for preparing a selected surface layer.
Figure 7:
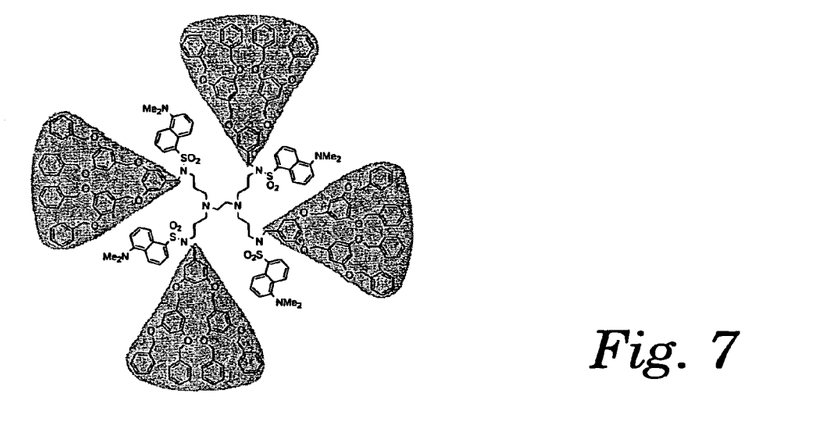
FIGS. 7-12 shows examples of dendrimers which are suitable for the preparation of selective surface layers.
Figure 8:
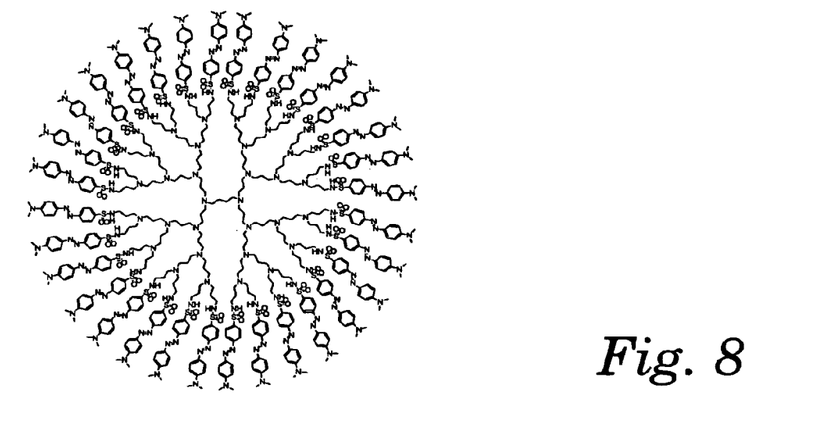
Figure 9:
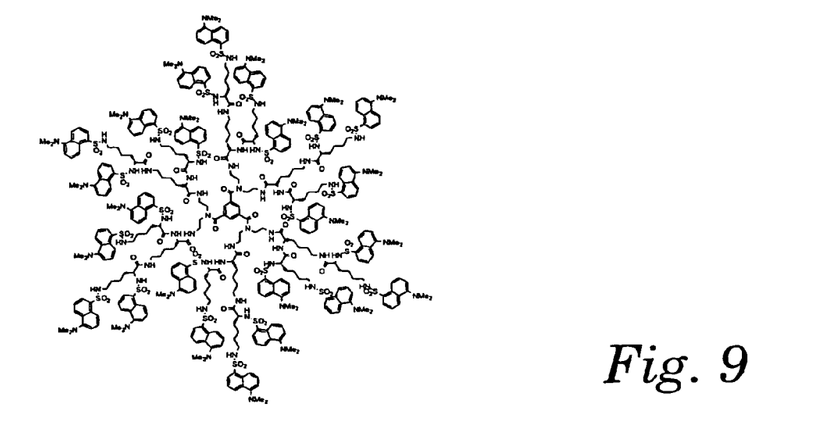
Figure 10:
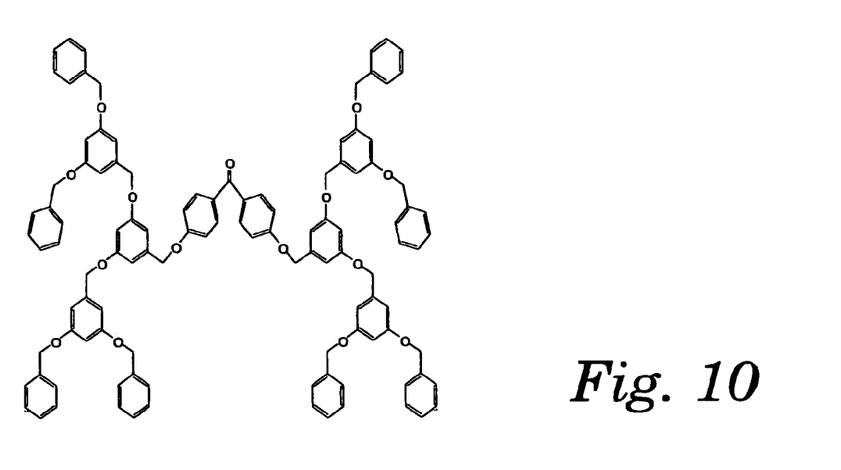
Figure 11:
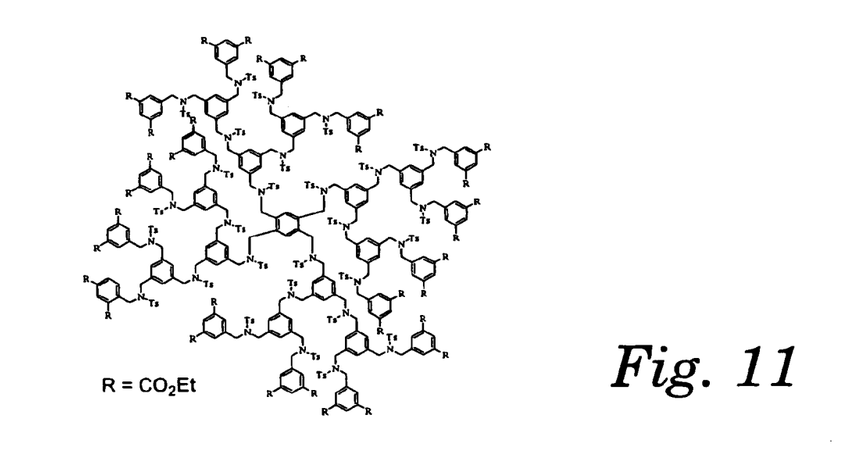
Figure 12:
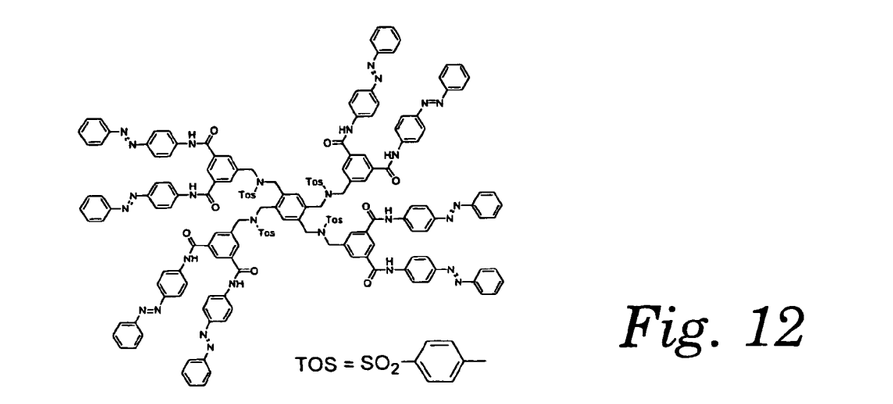

A host structure which is preorganized and capable of hydrogen bonds owing to amide groups has proved to be a particularly suitable sensor-active layer. As an example of a circular molecule meeting these requirements, FIG. 6 shows the lactam macrocycle. The ring has four potential coordination centers in the form of amide, thioamide or sulfonamide groups.

Finally, preferred dendrimers for the preparation of selective surface layers which are suitable in particular for detecting MITC and/or 1,3-dichloropropene are shown in FIGS. 7 to 12.

EXAMPLE

A device for detecting methyl isothiocyanate (MITC) in air samples was prepared by providing six individual quartz microbalances (obtained with commercially available electronic circuitry from HKR Sensorsysteme GmbH, Munich, Germany) with a surface layer of a lactame amide type macrocycle denoted J1. The frequency of operation or oscillation was in the range of around 10 MHz.

Preparation of J1

J1, i.e. a lactame amide macrocycle of the form 31'-tert-butyl-5',19',25',37',40',42',45',47'-octamethyl-8',16',28',34'-tetraoxodispiro[cyclohexane-1,2'-[7',17', 27',35',]tetraaza[10']oxyheptacyclo[34.2.2.23',6'.218',21'.223'26'.111', 15'.129',33']-heptatetracontal[3',5',11',13',15'(41'),18',20', 23',25',29',31',33'(46'),36',38',39',42',44']octa-decaen-20', 1"-cyclohexane], was prepared as follows.

To a solution of 10.00 g (32.30 mmol) of 1,1-bis(4'-ammo-3',5'-dimethylphenyl)cyclohexane and 2.2 ml of triethylamine in 50 ml of absolute dichloromethane a solution of 3-phenoxyacetyldichloride in 100 ml absolute dichloromethane are was added dropwise at room temperature during a period of 5 hours under continuous stirring in a well heat-dried and argon-flushed apparatus. The resulting mixture was stirred over night, upon which the solvent was removed at reduced pressure using a rotary evaporator.

The residue was purified via column chromatography using silica. Upon that, 1,4 g (37%) of a colorless solid were obtained (Mp=149-151° C.). 1.20 g (1.50 mmol) thereof were dissolved together with 0.4 ml triethylamine in 250 ml of dichloromethane. Likewise, 0.39 g (1.50 mmol) of 5-tert-butyl isophthalic acid chloride were dissolved in 250 ml of dichloromethane. Both solutions were added synchronously during a period of 8 hours to 1 liter of the same solvent (dichloromethane) at room temperature. Thereafter, the reaction mixture was stirred for an additional 2 days, upon which the solvent was removed at reduced pressure. 0.47 g (32%) of a colorless solid were obtained upon chromatographic purification on silica (Mp>260° C.). This colorless solid has been identified to be J1 (with a composition and structure as outlined above) using Maldi-MS with m/z=991,2 [M$^+$], 1014,2 [M$^+$+Na], 1030,2 [M$^+$+K].

Preparation of Surface Layer

The J1 surface coatings are applied by electro-spraying a solution of J1 through a capillary of an appropriately dimensioned syringe onto the top electrode of each individual quartz microbalance(QMB), one at a time, while applying a high DC voltage of about 5 kV between the capillary and the top electrode of the QMB. The coating process was monitored in situ. The resulting thickness of the coating was standardized by terminating electro-spraying when the oscillating frequency was reduced by 5 kHz.

Results

Defined concentrations of MITC were obtained by bubbling a steady and defined stream of pure nitrogen through a melt of (MITC). Then, the stream was cooled down by means of an efficient cooling device maintained at a constant temperature of −12° C. Subsequently, this defined concentration of MITC in nitrogen was further diluted by mixing it with a defined stream of pure nitrogen to provide a stream of a variable concentration of MITC in nitrogen.

Streams having concentrations of MITC in nitrogen of 10, 25, 50, 100, or 200 ppm were fed at 22 ml/min via suction through a measuring chamber housing the QMB array. The QMBs as well as the measuring chamber were maintained at 35° C. A reduction of oscillating frequencies of the individual QMBs proportional to the MITC concentration was observed, namely a reduction of 2.5, 7.0, 14.0, 24.0, and 37.5 Hz, respectively.

Accordingly, MITC concentrations in the range of a few ppm can be detected accurately and reproducibly with the device of the present invention.

We claim:

1. A method for detecting methyl isothiocyanate in soil air samples, comprising:
   drawing in a soil air sample;
   bringing the drawn-in soil air sample into contact with at least one mass-sensitive sensor comprising at least one quartz microbalance;
   detecting mass changes of the sensor in the form of electrical signals; and
   evaluating the electrical signals to detect a change in mass of methyl isothiocyanate;
   wherein:
   the quartz micro-balance is coated with a surface layer that is selective for incorporation of methyl isothiocyanate; and
   the quartz micro-balance comprises macrocycles and calibrated to detect methyl isothiocyanate.

2. A method as claimed in claim 1, wherein the at least one mass-sensitive sensor comprises a plurality of sensors coated with different selective layers.

3. A method as claimed in claim 1, wherein the methyl isothiocyanate to be detected is concentrated before making contact with the mass-sensitive sensor.

4. A method as claimed in claim 1, further comprising determining the moisture content of the air sample.

5. A method as claimed in claim 1, wherein moisture is removed from the air sample before it is brought into contact with the sensor.

6. A method of controlling phytopathogens, comprising:
   treating soil with an effective amount of a methyl thioisocyanate generating fumigant; and
   detecting residual amounts of released methyl isothiocyanate by the method of claim 1 before proceeding with new sowings or plantings of useful plants or crop plants in the soil.

\* \* \* \* \*